(12) United States Patent
Phillips et al.

(10) Patent No.: US 11,969,382 B2
(45) Date of Patent: Apr. 30, 2024

(54) SYSTEM AND METHOD FOR REDUCING AIRBORNE MICROBES

(71) Applicant: ZENTOX CORPORATION, Newport News, VA (US)

(72) Inventors: Joe D. Phillips, Barhamsville, VA (US); Stephen P. Axtell, Charlotte, NC (US)

(73) Assignee: ZENTOX CORPORATION, Newport News, VA (US)

( * ) Notice: Subject to any disclaimer, the term of this patent is extended or adjusted under 35 U.S.C. 154(b) by 0 days.

(21) Appl. No.: 15/506,668

(22) PCT Filed: Aug. 26, 2015

(86) PCT No.: PCT/US2015/046996
§ 371 (c)(1),
(2) Date: Feb. 24, 2017

(87) PCT Pub. No.: WO2016/033216
PCT Pub. Date: Mar. 3, 2016

(65) Prior Publication Data
US 2017/0273845 A1    Sep. 28, 2017

Related U.S. Application Data

(60) Provisional application No. 62/041,992, filed on Aug. 26, 2014.

(51) Int. Cl.
*A61G 12/00* (2006.01)
*A61G 13/10* (2006.01)
*A61L 9/20* (2006.01)

(52) U.S. Cl.
CPC ......... *A61G 12/008* (2013.01); *A61G 13/108* (2013.01); *A61L 9/205* (2013.01); *A61L 2209/16* (2013.01)

(58) Field of Classification Search
CPC ..... A61G 12/008; A61G 13/108; A61L 9/205; A61L 2209/16; A61L 9/20; F24F 3/163;
(Continued)

(56) References Cited

U.S. PATENT DOCUMENTS 5,267,895 A * 12/1993 Mitchell ................. F24F 3/163
454/57
5,834,069 A * 11/1998 Berman ............. B01D 53/8668
427/553
(Continued)

FOREIGN PATENT DOCUMENTS

JP      2013103032      *  5/2013

OTHER PUBLICATIONS

Barrick et al., "Special Department HVAC Issues: Operating Rooms", www.ashe.org/complinace/ec_02_01/01/secia;dept_or.shtml, an excerpt from Mechanical Systems Handbook for Health Care Facilities, 2014.*

(Continued)

*Primary Examiner* — Xiuyu Tai
(74) *Attorney, Agent, or Firm* — Lewis Roca Rothgerber Christie LLP

(57) ABSTRACT

Systems and methods of reducing airborne contaminants, such as airborne microorganisms, including bacterial, viral, and fungal microbes, in an indoor space are disclosed. The method includes positioning a portable photo-catalytic oxidation system proximate a source of contaminants in the indoor space and activating the photo-catalytic oxidation system to circulate air through the photo-catalytic oxidation system at a rate ranging from approximately 16 to approximately 24 air exchanges per hour in the indoor space. The photo-catalytic oxidation system is configured to oxidize contaminates in the air.

11 Claims, 3 Drawing Sheets

(58) Field of Classification Search
CPC ............... A47B 2200/06; F25D 17/042; F25D 2317/0417; B01D 2255/802; B01D 2259/804; B01D 53/007; B01D 53/885
See application file for complete search history.

(56) References Cited

U.S. PATENT DOCUMENTS

| | | | |
|---|---|---|---|
| 7,674,436 B1 | 3/2010 | Feldman et al. | |
| 7,820,100 B2 * | 10/2010 | Garfield | A61L 9/205 250/455.11 |
| 8,328,917 B2 | 12/2012 | Garfield et al. | |
| 2008/0152548 A1 * | 6/2008 | Clark | A61L 9/205 422/121 |
| 2009/0280027 A1 * | 11/2009 | Hayman, Jr. | A61L 9/205 422/4 |
| 2011/0171080 A1 | 7/2011 | Lo | |
| 2012/0199003 A1 * | 8/2012 | Melikov | A61G 10/02 95/273 |
| 2013/0085609 A1 * | 4/2013 | Barker | H05B 47/115 700/276 |
| 2014/0044591 A1 | 2/2014 | Phillips et al. | |
| 2014/0154133 A1 | 6/2014 | Lee | |
| 2015/0267429 A1 * | 9/2015 | Wall | E04H 3/08 52/173.1 |

OTHER PUBLICATIONS

Bhatia, "HVAC Design for Healthcare Facilities", Continuing Education and Development, Inc., Course No. M606-011, no date.*

Briller, "Patients and Urgency: Strategies for Designing Sustainable and Energy-efficient Hospitals for the 21st Century", Journal Energy Engineering, vol. 111, Issue 6, pp. 22-80, 2014.*

International Search Report and Written Opinions for International Application No. PCT/US2015/046996, dated Dec. 1, 2015, 12 pages.

* cited by examiner

SYSTEM AND METHOD FOR REDUCING AIRBORNE MICROBES

CROSS-REFERENCED TO RELATED APPLICATIONS

This application is a National Phase Patent Application and claims priority to and the benefit of International Application No. PCT/US2015/046996, filed on Aug. 26, 2015, which claims priority to and the benefit of U.S. Provisional Application No. 62/041,992, filed Aug. 26, 2014, the entire contents of both of which are incorporated herein by reference.

FIELD

The present disclosure relates to a system and method for reducing airborne contaminants in an indoor space.

BACKGROUND

Individuals suffering from a microbial infection (e.g., a bacterial, viral, or fungal infection) or a communicable disease are commonly admitted to a hospital for evaluation and treatment. These infected patients present a risk that they may spread and transmit their infection to other patients in the hospital. Airborne microbes are commonly spread through the central heating, ventilation, and air conditioning (HVAC) system in the hospital. For instance, a patient infected with a respiratory illness may expel microbes into the air by coughing or sneezing and these airborne microbes may then be circulated throughout the hospital by the HVAC system. Accordingly, many hospitals have retrofitted or outfitted their HVAC systems with filters designed to reduce the spread of contaminants throughout the hospital.

However, positioning the filters in the HVAC system limits the efficacy of the filters at reducing airborne microbes because the filters are remote from the source of the airborne microbes (e.g., an infected patient). Additionally, the air is typically cycled through the HVAC filters at a relatively slow rate, which further limits the efficacy of conventional filters in reducing the overall microbial load in the hospital. For instance, American Society of Heating, Refrigerating and Air-Conditioning Engineers (ASHRAE) Standard 170-2008 recommends six air exchanges per hour in a standard hospital patient room and ten air exchanges per hour in a standard bathroom in a hospital patient's room. A single air exchange occurs when the total volume of air in a room has been processed and/or treated once by the filtration system. Additionally, conventional filters in central HVAC systems are single pass systems because the air is passed through the HVAC system only once before being distributed throughout the building, which further limits the efficacy of these conventional HVAC filters.

SUMMARY

Embodiments of the present disclosure are directed to various methods for reducing airborne contaminants (e.g., airborne microbes) in an indoor space or area. In one embodiment, the method includes positioning a portable photo-catalytic oxidation (PCO) system proximate a source of contaminants in the indoor space and activating the PCO system to circulate air through the PCO system at a rate sufficient to perform from approximately 16 to approximately 32 air exchanges per hour in the indoor space. The PCO system is configured to oxidize contaminates in the air. The indoor space may be a hospital room and positioning the PCO system may include positioning the PCO system proximate a patient's hospital bed in the hospital room. Positioning the PCO system may include positioning the PCO system proximate a foot of the patient's hospital bed. Positioning the PCO system may include positioning the PCO system between the hospital bed and an entrance door of the hospital room. Positioning the PCO system may include positioning the PCO system between the hospital bed and a return air duct in the hospital room. The PCO system may have an airflow capacity of at least approximately 500 cubic feet per minute (CFM) and the indoor area may have a volumetric size from approximately 935 ft$^3$ to approximately 1875 ft$^3$. The indoor area may be an open system. The PCO system may include a support medium having a minimum efficiency reporting value (MERV) rating from approximately 10 to approximately 12 and a photocatalyst on the support medium. The support medium may be pleated and may be a fibrous matte. The photocatalyst may be titanium dioxide and may also include platinum.

Embodiments of the present disclosure are also directed to various systems for reducing airborne contaminants (e.g., airborne microbes) in an indoor space or area. In one embodiment, the system includes a portable photo-catalytic oxidation (PCO) system proximate a source of contaminants in the indoor space. Activation of the PCO system is configured to circulate air through the PCO system at a rate sufficient to perform approximately 16 to approximately 32 air exchanges per hour in the indoor space. The PCO system is configured to oxidize contaminants in the air. A ratio of an airflow capacity of the PCO system to a volumetric size of the indoor space may be from approximately 0.25 to approximately 0.5. The indoor space may have a volumetric size from approximately 935 ft$^3$ to approximately 1875 ft$^3$. The PCO system may have an airflow capacity of at least approximately 500 cubic feet per minute. The indoor space may be an open system hospital room. The PCO system may include a support medium having a minimum efficiency reporting value (MERV) rating from approximately 10 to approximately 12 and a photocatalyst on the support medium. The support medium may be pleated and may be a fibrous matte. The photocatalyst may be titanium dioxide and may also include platinum. The PCO system may be proximate a foot of a hospital bed in a hospital room, may be positioned between the hospital bed and an entrance door of the hospital room, and/or may be positioned between the hospital bed and a return air duct in the hospital room.

This summary is provided to introduce a number of concepts that are further described below in the detailed description. This summary is not intended to identify key or essential features of the claimed subject matter, nor is it intended to be used in limiting the scope of the claimed subject matter.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

The present disclosure relates to various methods of reducing airborne contaminants, such as airborne microbes (e.g., bacteria, viruses, and/or fungi), in a room or other indoor space (e.g., a hospital room, a home, a store, an office building, an airplane cabin, a cruise line, or a transportation vehicle) with a photo-catalytic oxidation (PCO) system. The circulation rate of the air through the PCO system and the proximity of the PCO system to a patient infected with a microbial infection or a communicable disease may be selected to optimize the efficacy of the PCO system in reducing the overall microbial load in the room. Reducing the microbial load in the room mitigates the risk that the airborne microbes will spread and infect other individuals. For instance, the methods of the present disclosure may be used to reduce the incidence of healthcare associated infections (HAI), which are infections acquired by patients during the course of receiving healthcare treatment for an unrelated ailment or condition. Additionally, the methods of the present disclosure may include positioning the PCO system proximate the source of the airborne microbes and operating the PCO system as a multi-pass system in which the air is repeatedly treated before the air is recirculated throughout the building.

Figure 1:
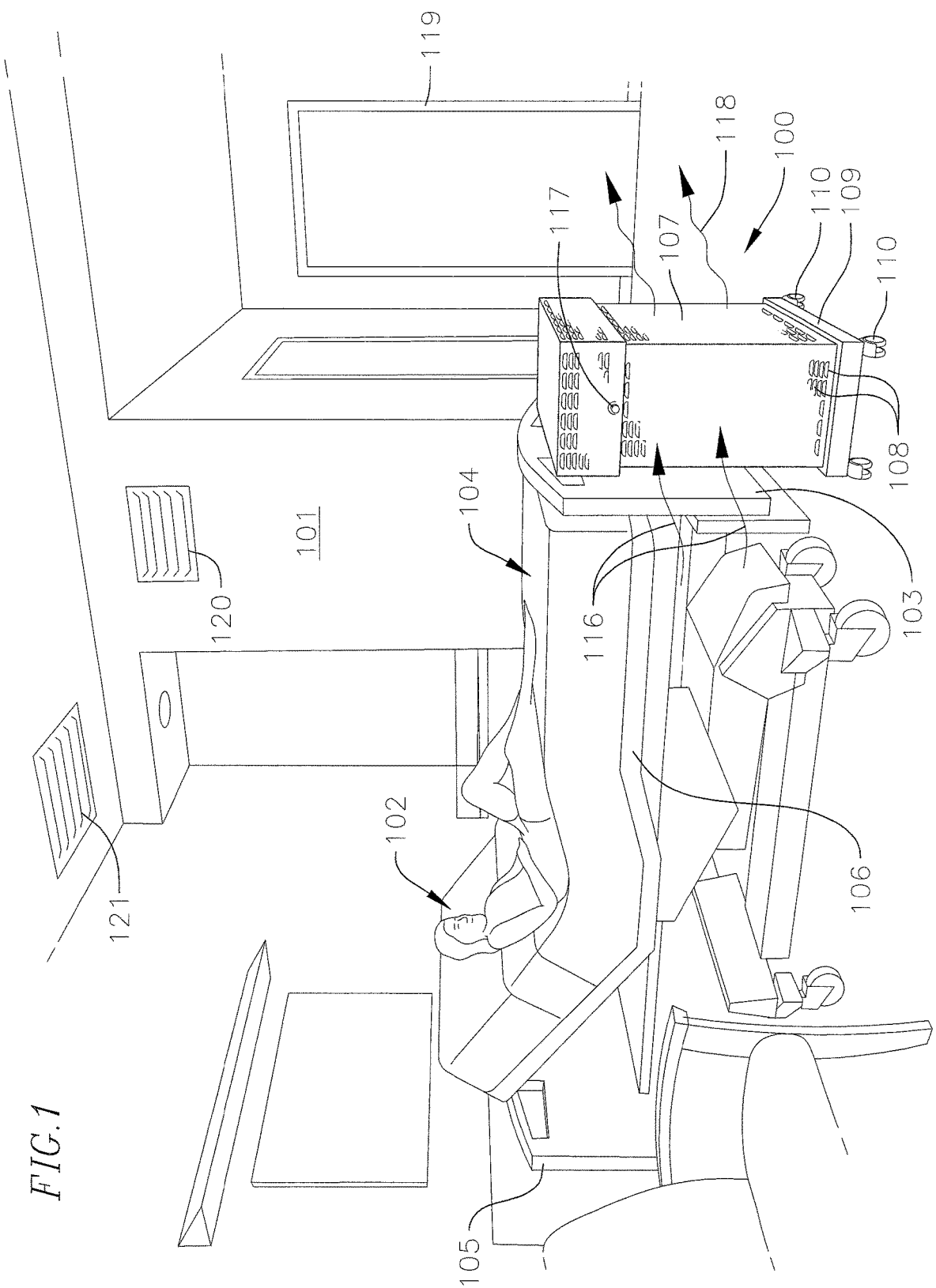
FIG. 1 is a perspective view of a photo-catalytic oxidation system treating air proximate to a foot of a hospital patient's bed in accordance with one method of the present disclosure for reducing airborne microbes.

With reference now to FIG. 1, a method of reducing airborne microbes (e.g., bacteria, viruses, and/or fungi) in an indoor space or area (e.g., a room) according to one embodiment of the present disclosure includes positioning a photo-catalytic oxidation (PCO) system 100 proximate a source of airborne microbes (i.e., a source of contaminants). In the illustrated embodiment, the PCO system 100 is positioned in a hospital room 101 (e.g., an emergency department patient room) proximate a patient 102 infected with a microbial infection (e.g., a bacterial, viral, and/or fungal infection) or a communicable disease. In one or more alternate embodiments, the PCO system 100 may be positioned in any other suitable environment in which it is desired to reduce airborne microbes, such as, for instance, in residential rooms, commercial office buildings, or industrial buildings. Additionally, in the illustrated embodiment, the PCO system 100 is positioned proximate a foot 103 of the patient's hospital bed 104. In one or more alternate embodiments, the PCO system 100 may be positioned at any other suitable location in the hospital room 101, such as, for instance, proximate a head 105 of the patient's hospital bed 104, or along one side 106 of the patient's hospital bed 104. In one or more alternate embodiments, the PCO system 100 may be positioned near any other source of airborne contaminants. Additionally, although in the illustrated embodiment only a single PCO system 100 is positioned in the room 101, in one or more alternate embodiments, a plurality of PCO systems 100 may be positioned within the room 101 to accelerate the process of reducing the airborne microbial load in the room 101. In one embodiment, the PCO system 100 is positioned a smaller distance from an exit/entrance doorway 119 of the hospital room 101 than is the patient's 102 mouth when the patient 102 is in the hospital bed 104, and may be placed substantially between the exit/entrance doorway 119 and the patient 102 (e.g., the patient's mouth) when the patient 102 is in the hospital bed 104. In one embodiment, the PCO system 100 is positioned between the patient 102 in the hospital bed 104 and a central heating, ventilation, and air conditioning (HVAC) return air duct 120 in the hospital room 101 that is configured to provide air to the hospital room 101. Additionally, in one embodiment, the PCO system 100 is positioned substantially between the patient 102 in the hospital bed 104 and an HVAC outlet duct 121 configured to intake air from the hospital room 101 and to distribute and/or recirculate the air throughout the hospital.

With continued reference to the embodiment illustrated in FIG. 1, the PCO system 100 includes a housing 107 defining a plurality of ducts or vents 108. In the illustrated embodiment, the PCO system 100 also includes a base 109 coupled to a lower end of the housing 107 and a plurality of wheels 110 coupled to the base 109. Accordingly, in the illustrated embodiment, the PCO system 100 is a portable PCO system that facilitates repositioning the PCO system 100 within the room 101 (e.g., repositioning the PCO system 100 around the patient's hospital bed 104) and/or moving the PCO system 100 between different rooms 101 depending on the nature of the conditions afflicting the various patients in the hospital. For instance, the portable PCO system 100 may be wheeled from one room in which the patient 102 is not suffering from an infectious disease and into a patient room 101 in which the patient 102 is suffering from an infectious disease or condition (e.g., a bacterial, viral, or fungal infection). In one or more alternate embodiments, the PCO system 100 may be a permanent or fixed PCO system located proximate the source of airborne microbes (e.g., the PCO system 100 may be a permanent PCO system located proximate the hospital bed 104).

Figure 2A:
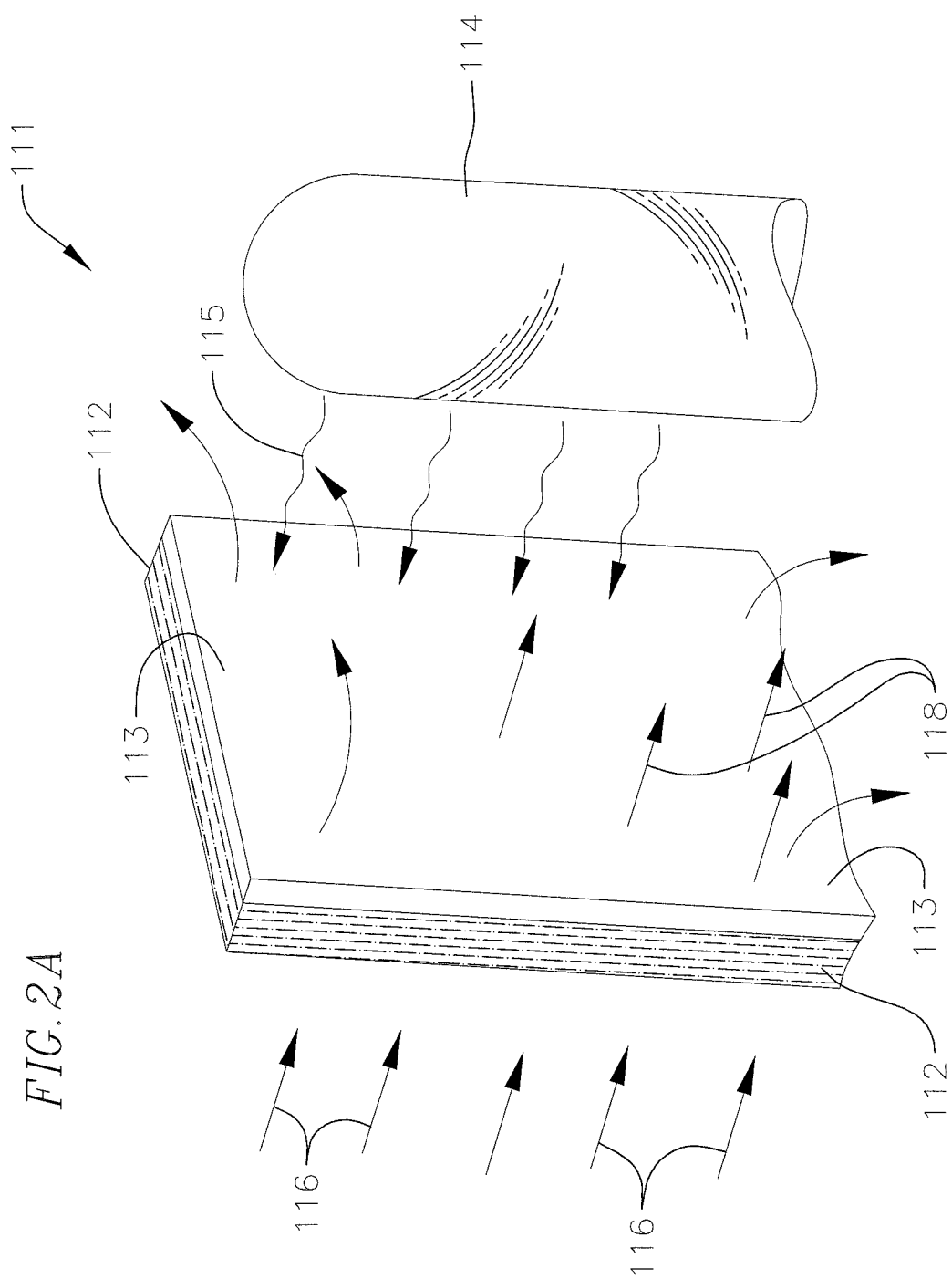
FIG. 2A is a perspective view of a photo-catalytic oxidation system according to one embodiment of the present disclosure.
Figure 2B:
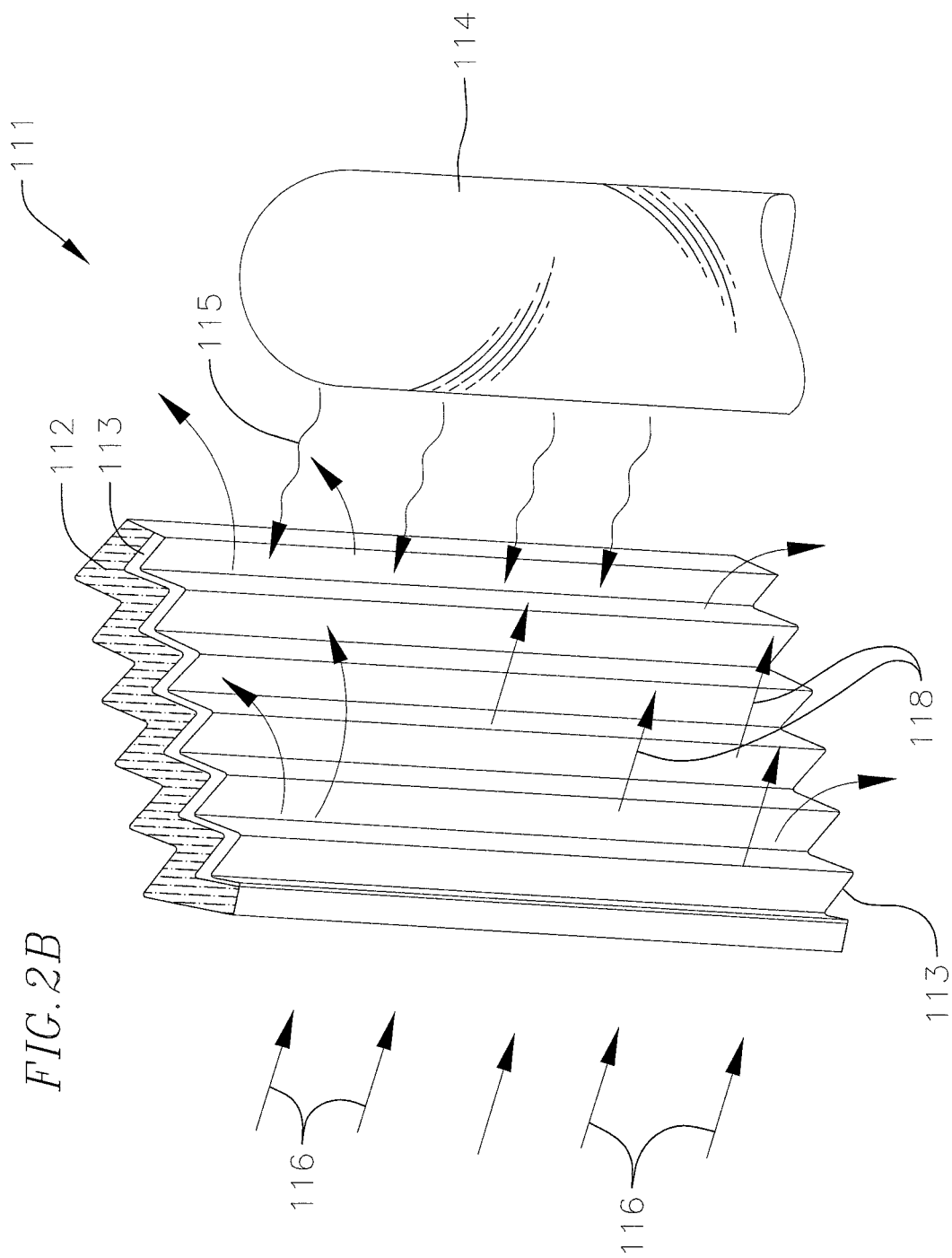
FIG. 2B is a perspective view of a photo-catalytic oxidation system according to another embodiment of the present disclosure.

With reference now to the embodiment illustrated in FIGS. 2A and 2B, the housing 107 of the PCO system 100 defines a chamber housing a PCO filter 111. In the illustrated embodiment, the PCO filter 111 includes a support medium 112, a photocatalyst 113 on the support medium 112, and an ultraviolet (UV) light source 114 configured to irradiate the photocatalyst 113 with UV light beams 115. The irradiation of the photocatalyst 113 with the UV light beams 115 is believed to produce hydroxyl radicals and super-oxide ions and/or other species that are highly reactive with volatile organic compounds (VOCs) (e.g., formaldehyde and ammonia), bacterial microbes, viral microbes, and fungal microbes. The PCO system 100 also houses a variable speed rate fan configured to draw contaminated air 116 in the room 101 through the PCO system 100. In one embodiment, the fan is configured to draw approximately 500 ft$^3$/min ("CFM") of contaminated air 116 through the PCO system 100. In one embodiment, the fan is configured to draw a maximum of approximately 500 ft$^3$/min ("CFM") of contaminated air 116 through the PCO system 100, although in one or more alternate embodiments, the fan may have any other capacity suitable for the size of the room 101 in which the PCO system 100 is intended to be operated, such as, for instance, greater than approximately 500 ft$^3$/min or less than approximately 500 ft$^3$/min (e.g., approximately 100 ft$^3$/min). The housing 107 of the PCO system 100 also includes control module or control knob 117 (see FIG. 1) configured to permit an operator to select the desired speed of the fan. As the contaminated air 116 is drawn through the PCO system 100 by the fan, the VOCs and/or microbes in the airstream 116 are oxidized (i.e., degraded) as they are adsorbed on the surface of the photocatalyst 113. In this manner, the PCO system 100 is configured to produce purified air 118. The fan is also configured to expel the purified air 118 out through the ducts or vents 108 in the housing 107 and into the room 101. In this manner, the air in the patient room 101 is purified before the air passes to the remainder of the hospital by the central heating, ventilation, and air conditioning (HVAC) outlet vent 121 (see FIG. 1), which reduces the incidence of the airborne microbes spreading and infecting other patients in the hospital.

In one embodiment, the volumetric size of the room 101 and the airflow capacity of the PCO system 100 may be selected such that the PCO system 100 is sufficiently sized relative to the hospital room 101 to perform from approximately 16 to approximately 32 air exchanges per hour, such as, for instance, approximately 24 air exchanges per hour. The airflow capacity of the PCO system 100 is a function of the fan speed, the size of the PCO filter 111, and the air permeability rating ("APR") of the PCO filter 111, described below. A single air exchange occurs when the total volume of air in the room 101 has been treated once by the PCO system 100. For instance, in an embodiment in which the PCO system 100 is operating at an airflow capacity of approximately 500 ft$^3$/min and the room 101 has a volumetric size of approximately 1250 ft$^3$, the PCO system 100 is configured to perform approximately 24 air exchanges per hour. In one embodiment, a ratio of the airflow capacity of the PCO system 100 to the volumetric size of the room 101 may be from approximately 0.25 to approximately 0.55, such as, for instance, approximately 0.4 (e.g., the PCO system 100 may be positioned in a room 101 having a volumetric size such that the PCO system 100 is configured to perform from approximately 0.25 to approximately 0.55 air exchanges per minute). In one embodiment, the method may include operating the PCO system 100 in a room 101 having a volumetric size from approximately 935 ft$^3$ to approximately 1875 ft$^3$. In one or more alternate embodiments, the airflow capacity of the PCO system 100 and the size of the room 101 in which the PCO system 100 is operating may be selected such that the PCO system 100 is configured to perform any other suitable number of air exchanges per hour depending on a variety of factors, including the desired rate of oxidation (i.e. degradation) of the VOCs and airborne microbes in the air and the initial microbial load in the room 101.

The support medium 112 may be a silica-based fibrous matte (e.g., fiberglass) or other suitable support material to which the photocatalyst 113 is adhered. The photocatalyst 113 may be adhered to the support medium 112 in any suitable manner, such as, for example, as described in U.S. Pat. Nos. 5,766,455 and 5,834,069, the entire contents of both of which are hereby incorporated by reference. The photocatalyst 113 on the support medium 112 may be a semiconductor catalyst such as a transition metal oxide, for example titanium dioxide or other suitable material. Additionally, the photocatalyst 113 may be metalized or non-metalized. The photocatalyst 113 may be metalized with any suitable metal such as, for example, a noble metal, such as platinum and/or palladium. The addition of platinum on the photocatalyst 113 is configured to accelerate the oxidation process. The metal may be deposited on the photocatalyst 113, if desired, before the photocatalyst 113 is applied to the support medium 112.

In one embodiment, the support medium 112 has a minimum efficiency reporting value (MERV) rating in a range from approximately 10 to approximately 12, although in one or more alternate embodiments, the support medium 112 may have any other suitable MERV rating. Additionally, in one embodiment, the support medium 112 is composed of loosely-packed fibers such that the support medium 112 has an air permeability rating ("APR") of greater than approximately 155 CFM/ft$^2$, such as, for instance, at least approximately 200 CFM/ft$^2$ or at least approximately 247 CFM/ft$^2$. Loosely packing the fibers of the support medium 112 is configured to reduce the pressure drop of the air across the support medium 112, which allows the air to pass more quickly through the support medium 112. The increased rate of air circulation through the PCO system 100 exposes the airborne microbes or other contaminants in the air to the active photocatalyst sites on the support medium 112 more frequently, and thus the airborne microbes or other contaminants are oxidized (i.e., degraded) more rapidly than with an otherwise comparable PCO filter having a lower air permeability rating. In one or more alternate embodiments, the support medium 112 may be composed of densely-packed fibers such that the support medium 112 has an APR of approximately 155 CFM/ft$^2$ or less.

With continued reference to the embodiments illustrated in FIGS. 2A and 2B, the support medium 112 of the PCO filter 111 may have any suitable shape, such as, for instance, a flat, rectangular shape (i.e., a rectangular prism) (see FIG. 2A) or a pleated shape (see FIG. 2B). The pleats increase the surface area of the support medium 112 such that the pleated support medium 112 is configured to support more photocatalyst 113 than an otherwise comparable flat, rectangular support medium 112 having the same peripheral linear dimensions (i.e., height and width) as the pleated support medium 112. Accordingly, the greater number of active catalytic sites on the pleated support medium 112 enables a PCO system 100 incorporating the pleated support medium 112 to oxidize (i.e., degrade) contaminants in the air more quickly than a PCO system 100 incorporating a flat support medium 112 having a smaller surface area and therefore fewer active catalytic sites. PCO filters suitable for use with the methods of the present disclosure are described in U.S. patent application Ser. No. 13/963,988, entitled "Photocatalytic Oxidation Media and System," and filed Aug. 9, 2013, the entire content of which is incorporated herein by reference.

Tests were performed to determine the efficacy of the methods of the present disclosure in reducing airborne microbial loads. The PCO systems 100 of the present disclosure were placed proximate the foot 103 of hospital beds 104 in a number of patient rooms within one emergency department that housed fifty different patients over the course of the testing period. Prior to activating the PCO systems 100, the air in each room 101 was tested to establish the baseline microbial load in each of the rooms 101. The baseline air sampling was performed using three 6-stage Andersen samplers positioned at the head 105 and the foot 103 of the hospital beds 104 and at an exit/entrance doorway 119 of each hospital room 101. The air samples were collected on blood agar plates.

Following completion of the baseline air sampling, the PCO systems 100 proximate the foot 103 of the hospital beds 104 were activated to circulate the contaminated air 116 in the room 101 through the PCO system 100. The air 116 was circulated through the PCO system 100 for approximately 20 minutes before beginning air sampling to determine the reduction in microbial load in the rooms 101. In one embodiment, the PCO system 100 had a maximum capacity of approximately 500 ft$^3$/minute and the rooms 101 had a volumetric size of approximately 1250 ft$^3$ such that approximately 8 air exchanges occurred within the 20-minute period prior to sampling (i.e., a rate of approximately 24 air exchanges per hour). A single air exchange occurs when the total volume of air in the room 101 has been treated once by the PCO system 100. After the air 116 was treated by the PCO systems 100 for approximately 20 minutes, the air was sampled again with the three 6-stage Anderson samplers in each room 101. Once the samples were collected, the blood agar plates were removed from the Anderson samplers and placed in an incubator at approximately 37° C. The plates were incubated for approximately 48 hours and then the number of colonies formed on the agar plates were calculated and recorded.

The results of the tests are summarized below in Table 1. For each location, the colony count was summed across the 6 stages of the Anderson samplers. The results are presented as median values across each of the tested rooms and as interquartile ranges (i.e., the 25th and 75th quartiles) shown in parentheses following the median value. Table 1 also indicates the number of patients (N) whose rooms were sampled for each of the three locations of the PCO system 100 in the room 101. The p-values were determined using the signed Wilcoxon rank-sum test.

TABLE 1

|  | Baseline No. of Colonies | Post-Treatment Number of Colonies | Difference | P-Value | Percentage Difference | N |
|---|---|---|---|---|---|---|
| Head of Bed | 14 (7 to 24) | 5.5 (3 to 12) | −7 (−17.75 to 0) | ≤0.001 | −54.17% (−70.00% to −5.36%) | 48 |
| Foot of Bed | 11.5 (6 to 24.25) | 7 (4 to 13.75) | −4.5 (−12.5 to −3) | ≤0.001 | −46.9% (−66.67% to −31.41%) | 48 |
| Exit of Room | 9.5 (4.25 to 22) | 7 (3.25 to 13.75) | −3.5 (−10.75 to −1.75) | 0.002 | −26.67% (−75.00% to −15.79%) | 49 |
| Total | 38.5 (21 to 68.75) | 20 (13.25 to 37.75) | −15 (−36.75 to −1) | ≤0.001 | −46.00% (−66.86% to −15.73%) | 49 |

Accordingly, operation of the PCO systems 100 at the feet 103 of the hospital beds 104 for approximately 20 minutes reduced the microbial load at the heads 105 of the hospital beds 104 by approximately 54.2%. Operation of the PCO systems 100 at the feet 103 of the hospital beds 104 for approximately 20 minutes also reduced the microbial load at the feet 103 of the beds 104 by approximately 46.9% and at the exit/entrance doors 119 of the rooms 101 by approximately 26.7%. The lower reduction in the microbial load at the exit/entrance door 119 may be due to higher personnel traffic and activity through and/or around the exit/entrance door 119 of the room 101 compared to the foot 103 and the head 105 of the hospital beds 104. That is, unlike a clean room or other sterile controlled environments, the patient rooms 101 were open systems in which personnel and other individuals were permitted to freely enter and exit the rooms 101 through the doorway 119 during the tests.

Although in one or more embodiments the PCO systems 100 of the present disclosure may be used to reduce airborne contaminants (e.g., airborne microbes) in a hospital room, in one or more embodiments, the PCO systems 100 of the present disclosure may be used to reduce airborne contaminants, such as airborne microbes (e.g., bacteria, viruses, and/or fungi), in any other type of room or other indoor space or area, such as, for instance, in homes, stores, office buildings, airplane cabins, cruise lines, and transportation vehicles (i.e., the PCO systems 100 of the present disclosure may be used in any indoor space in which airborne contaminants are desired to be reduced).

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims. Although relative terms such as "outer," "inner," "upper," "lower," "below," "above," "vertical," "horizontal," and similar terms have been used herein to describe a spatial relationship of one element to another, it is understood that these terms are intended to encompass different orientations of the various elements and components of the invention in addition to the orientation depicted in the figures. Additionally, as used herein, the term "substantially" and similar terms are used as terms of approximation and not as terms of degree, and are intended to account for the inherent deviations in measured or calculated values that would be recognized by those of ordinary skill in the art. Moreover, the tasks described above may be performed in the order described or in any other suitable sequence. Additionally, the methods described above are not limited to the tasks described. Instead, for each embodiment, one or more of the tasks described above may be absent and/or additional tasks may be performed. Furthermore, as used herein, when a component is referred to as being "on" another component, it can be directly on the other component or components may also be present therebetween. Moreover, when a component is referred to as being "coupled" to another component, it can be directly attached to the other component or intervening components may be present therebetween.

What is claimed is:

1. A method of reducing airborne contaminants in air of an indoor space, the method comprising:
    positioning an individual, portable photo-catalytic oxidation system proximate a source of contaminants in the indoor space;
    activating the individual, portable photo-catalytic oxidation system to recirculate all of the air in the indoor space through the individual, portable photo-catalytic oxidation system in a multi-pass manner at a rate sufficient to perform from approximately 24 to approximately 32 air exchanges per hour of all of the air in the indoor space before distributing the air to another space, wherein the individual, portable photo-catalytic oxidation system is configured to oxidize contaminates in the air,
    wherein a ratio of an airflow capacity of the individual, portable photo-catalytic oxidation system to a volumetric size of the indoor space is in a range from 0.4 to approximately 0.5, and
    wherein the indoor space is a hospital room, and wherein the positioning of the individual, portable photo-catalytic oxidation system comprises positioning the individual, portable photo-catalytic oxidation system proximate to a head of the patient's hospital bed, between the patient's hospital bed and an outlet duct of a central heating, venting, and air conditioning (HVAC) unit of the hospital room, and between a side of the patient's hospital bed facing an exit/entrance doorway of the hospital room and the exit/entrance doorway of the hospital room.

2. The method of claim 1, wherein the individual, portable photo-catalytic oxidation system has an airflow capacity of at least approximately 500 cubic feet per minute.

3. The method of claim 1, wherein the individual, portable photo-catalytic oxidation system has an airflow capacity of approximately 500 cubic feet per minute.

4. The method of claim 1, wherein the individual, portable photo-catalytic oxidation system comprises:
- a support medium having a minimum efficiency reporting value (MERV) rating in a range from approximately 10 to approximately 12;
- a photocatalyst on the support medium; and
- an ultraviolet light source configured to irradiate the photocatalyst with ultraviolet light.

5. The method of claim 4, wherein the support medium is pleated.

6. The method of claim 4, wherein the support medium is a fibrous matte.

7. The method of claim 4, wherein the photocatalyst is titanium dioxide.

8. The method of claim 7, wherein the photocatalyst further comprises platinum.

9. The method of claim 1, wherein the indoor space is an open system.

10. The method of claim 1, wherein the indoor space has a volumetric size from approximately 935 $ft^3$ to approximately 1875 $ft^3$.

11. The method of claim 1, wherein the positioning of the individual, portable photo-catalytic oxidation system further comprises positioning the individual, portable photo-catalytic oxidation system between the patient's hospital bed and an inlet duct of the HVAC unit of the hospital room.

* * * * *